US00PP18667P2

(12) United States Plant Patent
Bradford

(10) Patent No.: US PP18,667 P2
(45) Date of Patent: Mar. 25, 2008

(54) INTERSPECIFIC TREE NAMED 'PLUMSWEET VII'

(50) Latin Name: ***Prunus* sp.**
Varietal Denomination: Plumsweet VII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,859

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP13,476 P2 1/2003 Bradford

*Primary Examiner*—Kent Bell
*Assistant Examiner*—S. B. McCormick-Ewoldt

(57) ABSTRACT

The present invention relates to an interspecific tree and more particularly to a new and distinct variety broadly characterized by a large size, vigorous, hardy, and productive tree. Being self-unfruitful, the present variety requires cross pollination from an apricot, interspecific, or plum that blooms during the early season. The fruit matures under the ecological conditions described during late June, with first picking on Jun. 26, 2006. The fruit is uniformly medium in size, mostly red with greenish yellow freckling in skin color, clingstone in type, oblate in shape, red to pink in flesh color.

1 Drawing Sheet

Botanical classification: *Prunus* sp.
Varietal denomination: 'PLUMSWEET VII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'PLUMSWEET VII'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unnamed red plum was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "H5". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'YUMMYrosa' (U.S. Plant Pat. No. 13,476) plum by being self-unfruitful and by producing fruit that is medium in size, that is clingstone in type, and that matures in late June, but is distinguished therefrom by producing fruit that is firmer in texture, that is entirely red to pink in flesh color, that is more oblate in shape, that has abundant greenish yellow freckling, and that is somewhat sweeter in flavor.

SUMMARY OF VARIETY

The preset interspecific variety is characterized by a large size, vigorous, hardy, and productive tree. Being self-unfruitful, the present variety requires cross pollination from an apricot, interspecific, or plum that blooms during the early season. The present variety's abundance of blossoms and pollen entices strong bee activity to facilitate pollination. The fruit matures under the ecological conditions described during late June, with first picking on Jun. 26, 2006, and will hang on the tree for about fifteen more days. The fruit is uniformly medium in size, mostly red with greenish yellow freckling in skin color, clingstone in type, oblate in shape, red to pink in flesh color, very firm and crisp in texture, and outstanding in flavor.

DRAWING

The accompanying photograph consists of four whole fruits positioned to display the characteristics of the skin color and form, two halves of one fruit divided transversely to the suture plane to reveal the flesh and stone, typical leaves and an inset depicting the blossoms as they appear on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jun. 30, 2006, on the original tree during its fifth growing season. The flower and bud descriptions were developed during the previous blooming season. All major color code designations are by reference to the Inter-Society Color Council, National Bureau of Standards. Common color names are also used occasionally.

Parentage:
- *Seed parent.*—Unnamed red plum.
- *Pollen parent.*—Unknown.

Tree

Size: Large, reaching and maintaining a height of 13' [3.96 m.] and a spread of 9' [2.74 m.] after five growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to central leader form.

Hardiness: Hardy with respect to central California winters.

Heat tolerance: Observed to perform adequately in typical central California climatic conditions, which typically include extended periods of heat.

Drought tolerance. —Variety is developed for commercial orchards and requires regular irrigation.

Production: Medium productive, thinning usually required.

Fertility: Self-unfruitful, requiring cross pollination by a suitable early to mid seasonal blooming apricot, interspecific, or plum.

Bearing: Uncertain bearer, dependent upon favorable weather during the blooming period.

Trunk:
- *Size.*—Large, reaching a maximum diameter of 5" [127 mm.] after the fifth growing season.
- *Texture.*—Shaggy.
- *Bark color.*—A Dark grayish grown [62. d.gy.Br] and Dark reddish brown [44. d.rBr] variegation with Light yellowish brown [76. l.yBr] crevices present.
- *Lenticels.*—Approximate Number Per Square Inch: 8. Color: Deep orange yellow [69. deep OY]. Typical Size: 3/16" [4.8 mm.] to 9/16" [14.3 mm.]. Shape: Eye-shaped to elongated.

Branches:
- *Size.*—Diameter of first lateral is 1⅛" [29 mm.] measured 12" from the central leader.
- *Texture.*—Smooth on first and second year wood, increasing roughness with age.
- *Color.*—1st Year Wood Topside: Moderate brown [58. m.Br]. 1st Year Wood Underside: Brilliant yellow green [116. brill.YG]. Older Wood: Deep yellowish brown [75. green yBr].
- *Lenticels.*—Number Per Square Inch: More than 60 on second year wood. Color: Moderate orange yellow [71. m.OY]. Typical size: 1/32" [0.8 mm.] to 3/32" [2.4 mm.]. Shape: Elongated.

Leaves:
- *Size.*—Medium. Average Length: 3¾" [95 mm.]. Average width: 1 11/16" [43 mm.].
- *Arrangement.*—Alternate.
- *Thickness.*—Medium.
- *Form.*—Elliptical.
- *Apex.*—Acuminate.
- *Base.*—Acute with an average base angle of 65 to 75 degrees.
- *Surface.*—Smooth.
- *Color.*—Dorsal Surface: Dark olive green [126. d.OlG]. Ventral Surface: Moderate olive green [125. m.OlG].
- *Margin.*—Finely serrate.
- *Venation.*—Pinnately net veined.
- *Petiole.*—Average Length: ¾" [19.1 mm.]. Average Thickness: 1/16" [1.6 mm.]. Color: Dark reddish orange [38. d.rO] on the topside, Strong yellow green [117. s.YG] underneath.
- *Stipules.*—Number: 2 per leaf, up to 6 per growing tip. Average Length: ¼" [6.4 mm.]. Color: Strong yellow green [117. s.YG] becoming Moderate reddish brown [43. m.rBr] with age.
- *Glands.*—Number: 2 to 5 per leaf. Position: Both alternate and opposite, positioned on the petiole and base of blade. Size: Small. Form: Reniform when mature, appear globose when young. Color: Strong yellow green [117. s.YG] becoming Deep reddish brown [41. deep rBr] in the center with age.
- *Leaf buds.*—Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White].

Flowers: Perfect, complete, perigynous, usually a single pistil, typically twenty-four or more stamens, five sepals and petal locations alternately positioned.
- *Average flower diameter.*—1 1/16" [27.0 mm.].
- *Number of petals.*—Five, no double blossoms observed.
- *Petal shape.*—Oval to circular.
- *Petal margin.*—Smooth to slightly wavy.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White].
- *Anther color.*—Vivid yellow [82 v.Y].
- *Stigma color.*—Pale greenish yellow [104. p.gY].
- *Sepal color.*—Brilliant yellow green [116. brill.YG] with Dark yellowish pink [30. d.yPk] near the margins.
- *Sepal length.*—5/32" [4.0 mm.].
- *Sepal width.*—⅛" [3.2 mm.].
- *Average pistil length.*—⅝" [15.9 mm.].
- *Average stamen length.*—½" [12.7 mm.].
- *Fragrance.*—Moderate.
- *Pollen production.*—Moderate.
- *Blooming period.*—Early, a few days after 'Ambra' (unpatented).

*Onset of bloom.*—One percent on Feb. 14, 2006.
*Date of full bloom.*—Feb. 26, 2006.
*Duration of bloom.*—One to two weeks, dependent on ambient temperature.
*Bloom density.*—Very heavy.
*Number per cluster.*—2 to 9, average 4.

FRUIT

Maturity when described: Eating ripe, Jun. 29, 2005.
Date of first picking: Jun. 26, 2006.
Date of last picking: Jul. 10, 2006.
Size: Uniform, medium.
*Average diameter axially.*—2 5/16" [59 mm.].
*Average diameter across cheek plane.*—2 9/16" [65 mm.].
*Average diameter across suture plane.*—2½" [64 mm.].
*Typical weight.*—5.4 ounces [153 grams].
Form: Uniform, oblate, symmetrical.
*Longitudinal section form.*—Oblate to elliptical.
*Transverse section through diameter.*—Round.
Suture: An inconspicuous line located in a very shallow groove extending from the base to just beyond the apex, with a slight depression at the pistil point.
Ventral surface: Rounded, slightly lipped toward the base.
Lips: Equal.
Cavity: Flaring, circular, suture showing on one side.
*Depth.*—⅜" [9.5 mm.].
*Breadth.*—1 1/16" [27.0 mm.].
Base: Truncate.
Apex: Rounded to slightly truncate.
Pistil Point: An inconspicuous dot.
Stem: Medium.
*Average length.*—⅜" [9.5 mm.].
*Average width.*—⅛" [3.2 mm.].
Skin:
*Thickness.*—Medium.
*Surface.*—Smooth.
*Tenacity.*—Tenacious to flesh.
*Astringency.*—Slight.
*Tendency to crack.*—Slight.
*Color.*—Dark red [16. d.R] smoothly blending into a Dark reddish orange [38. d.rO] background with Dark greenish yellow [103. d.gY] freckling throughout.
*Bloom.*—Abundant.
Flesh:
*Color.*—Light yellowish pink [28. l.yPk] with Dark red [16. d.R] streaking next to the skin and stone.
*Surface of pit cavity.*—Covered with Dark red [16. d.R] fibers when twisted away from stone.
*Amygdalin.*—Moderate.
*Juice.*—Abundant, rich.
*Texture.*—Firm, crisp.
*Fibers.*—Abundant, fine.
*Ripens.*—Slightly earlier toward the apex.
*Flavor.*—A tasty blend of acid and sugar, typically 19 brix.
*Aroma.*—Slight.
*Eating quality.*—Outstanding.

STONE

Type: Clingstone.
Form: Oval.
Hilum: Narrow, oblong.
Base: Straight.
Apex: Acuminate, with a sharp ⅛" [3.2 mm.] tip.
Sides: Equal.
Surface: Rough throughout with one groove from base to apex on each side of the dorsal fin.
External color of stone: Moderate yellowish brown [77. m.yBr].
Pit wall color when cracked: Moderate brown [58. m.Br].
Cavity surface color: Light brown [57. l.Br].
Average pit wall thickness: 1/16" [1.6 mm.].
Average width: 11/16" [17.5 mm.].
Average length: 1¼" [31.8 mm.].
Average breadth: ⅜" [9.5 mm.].
Tendency to split: None observed.
Kernel:
*Form.*—Oval.
*Skin color.*—Dark orange yellow [72. d.OY] when freshly removed.
*Pellicle color.*—Dark yellowish brown [78. d.yBr].
*Vein color.*—Moderate yellowish brown [77. m.yBr].
*Taste.*—Bitter.
*Viable.*—Yes.
*Average width.*—½" [12.7 mm.].
*Average length.*—11/16" [17.5 mm.].
*Amygdalin.*—Abundant.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMYrosa' (U.S. Plant Pat. No. 13,476) plum by being self-unfruitful and by producing fruit that is medium in size, that is clingstone in type, and that matures in late June, but is distinguished therefrom by producing fruit that is firmer in texture, that is entirely red to pink in flesh color, that is more oblate in shape, that has abundant greenish yellow freckling, and that is somewhat sweeter in flavor.

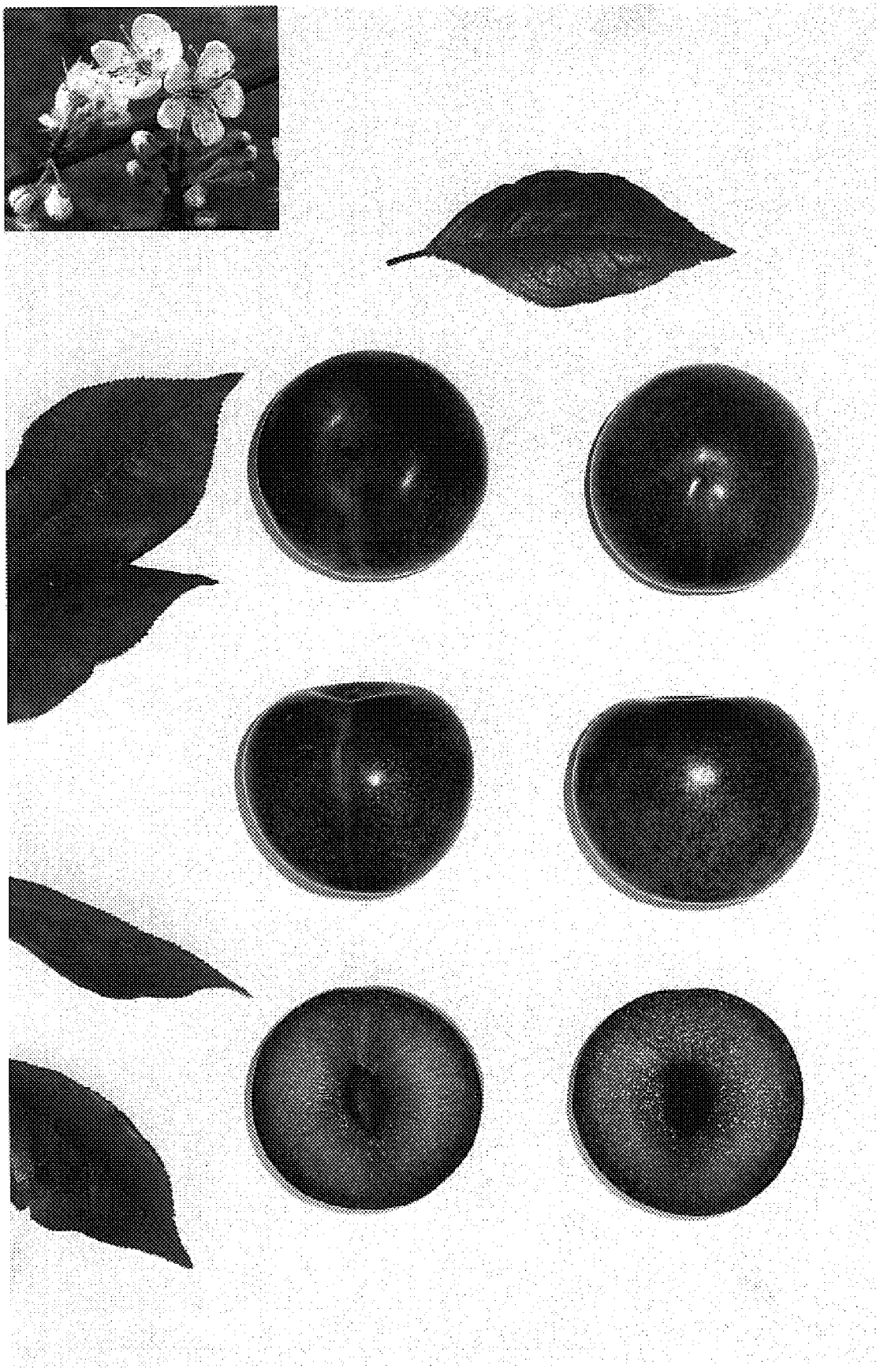

* * * * *